US011492653B2

(12) United States Patent
Thomson et al.

(10) Patent No.: US 11,492,653 B2
(45) Date of Patent: Nov. 8, 2022

(54) METHODS AND KITS FOR DETECTING ANTIBIOTIC-INACTIVATING FACTORS

(71) Applicant: University of Louisville Research Foundation, Inc., Louisville, KY (US)

(72) Inventors: Gina K. Thomson, Louisville, KY (US); Kenneth S. Thomson, Louisville, KY (US); Sameh Mohamed Mohamadi AbdelGhani, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 215 days.

(21) Appl. No.: 16/638,429

(22) PCT Filed: Aug. 14, 2018

(86) PCT No.: PCT/US2018/046775
§ 371 (c)(1),
(2) Date: Feb. 11, 2020

(87) PCT Pub. No.: WO2019/036516
PCT Pub. Date: Feb. 21, 2019

(65) Prior Publication Data
US 2020/0172953 A1    Jun. 4, 2020

Related U.S. Application Data

(60) Provisional application No. 62/657,429, filed on Apr. 13, 2018, provisional application No. 62/545,239, filed on Aug. 14, 2017.

(51) Int. Cl.
*C12Q 1/34* (2006.01)
*C12Q 1/18* (2006.01)

(52) U.S. Cl.
CPC .............. *C12Q 1/34* (2013.01); *C12Q 1/18* (2013.01); *G01N 2333/986* (2013.01)

(58) Field of Classification Search
None
See application file for complete search history.

(56) References Cited

U.S. PATENT DOCUMENTS

| 5,264,346 A | 11/1993 | Chen |
| 2005/0227309 A1 | 10/2005 | Corry et al. |
| 2009/0275065 A1 | 11/2009 | Xing et al. |
| 2011/0112059 A1 | 5/2011 | Hasan et al. |
| 2014/0080164 A1 | 3/2014 | Yang-Woytowitz et al. |
| 2014/0134656 A1 | 5/2014 | Dortet et al. |

OTHER PUBLICATIONS

Dortet, Laurent, et al. "Impact of the isolation medium for detection of carbapenemase-producing Enterobacteriaceae using an updated version of the Carba NP test." Journal of medical microbiology 63 (2014): 772-776. (Year: 2014).*

Webpage for Thermo Scientific B-PER II Bacterial Protein Extraction Reagent, accessed online on Dec. 13, 2021 at: https://www.thermofisher.com/order/catalog/product/78260.*

Webpage for Tryptic Soy Broth, accessed Dec. 13, 2021 at: https://assets.fishersci.com/TFS-Assets/LSG/manuals/IFU112730.pdf.*

AbdelGhani et al., "Comparison of the Carba NP, modified Carba NP, and updated Rosco Neo-Rapid Carb kit tests for carbapenemase detection," Journal of Clinical Microbiology, Nov. 1, 2015, 53(11):3539-42.

Doi et al., "Simple disk-based method for detection of Klebsiella pneumoniae carbapenemase-type β-lactamase by use of a boronic acid compound," Journal of Clinical Microbiology, Dec. 1, 2008, 46(12):4083-6.

Dortet et al., "CarbAcineto NP test for rapid detection of carbapenemase-producing *Acinetobacter* spp," Journal of Clinical Microbiology, Jul. 1, 2014, 52(7):2359-64.

Dortet et al., "Nordmann P. Rapid detection of carbapenemase-producing *Pseudomonas* spp," Journal of Clinical Microbiology, Nov. 1, 2012, 50(11):3773-6.

Dortet et al., "Rapid detection of carbapenemase-producing Enterobacteriaceae from blood cultures," Clinical Microbiology and Infection, Apr. 1, 2014, 20(4):340-4.

Dortet et al., "Rapid identification of carbapenemase types in *Enterobacteriaceae* and *Pseudomonas* spp by using a biochemical test," Antimicrobial Agents and Chemotherapy, Dec. 1, 2012, 56(12):6437-40.

Ehmann et al., "Kinetics of avibactam inhibition against class A, C, and D β-lactamases," Journal of Biological Chemistry, Sep. 27, 2013, 288(39):27960-71.

Garg et al., "Evaluation of the Rapidec Carba NP test kit for detection of carbapenemase-producing Gram-negative bacteria," Antimicrobial Agents and Chemotherapy, Dec. 1, 2015, 59(12):7870-2.

Huang et al., "Comparative evaluation of two chromogenic tests for rapid detection of carbapenemase in Enterobacteriaceae and in Pseudomonas aeruginosa isolates," Journal of Clinical Microbiology, Aug. 1, 2014, 52(8):3060-3.

Kabir et al., "A two-centre evaluation of RAPIDEC® CARBA NP for carbapenemase detection in *Enterobacteriaceae, Pseudomonas aeruginosa* and *Acinetobacter spp.*" Journal of Antimicrobial Chemotherapy, May 1, 2016, 71(5):1213-6.

Noël et al., "Comparative evaluation of four phenotypic tests for detection of carbapenemase-producing Gram-negative bacteria," Journal of Clinical Microbiology, Feb. 1, 2017, 55(2):510-8.

Nordmann et al., "Rapid detection of carbapenemase-producing Enterobacteriaceae," Emerging Infectious Diseases, Sep. 2012, 18(9):1503-7.

PCT International Preliminary Report on Patentability in International Appln. No. PCT/US2018/046775, dated Feb. 27, 2020, 7 pages.

PCT International Search Report in International Appln. No. PCT/US18/46775, dated Feb. 21, 2019, 7 pages.

Pires et al., "Blue-carba, an easy biochemical test for detection of diverse carbapenemase producers directly from bacterial cultures," Journal of Clinical Microbiology, Dec. 1, 2013. 51(12):4281-3.

(Continued)

*Primary Examiner* — Robert J Yamasaki
(74) *Attorney, Agent, or Firm* — Fish & Richardson P.C.

(57) ABSTRACT

Methods and compositions for detecting an antibiotic-inactivating factor produced by a microorganism are described herein.

9 Claims, 4 Drawing Sheets

(56) References Cited

OTHER PUBLICATIONS

Poirel et al., "Rapidec Carba NP test for rapid detection of carbapenemase producers," Journal of Clinical Microbiology, Sep. 1, 2015, 53(9):3003-8.

Takissian et al., "Test Carba 5 for rapid detection of carbapenemase-producing Enterobacterales from positive blood cultures," Antimicrobial Agents and Chemotherapy, May 1, 2019, 63(5):e00011-19.

Tamma et al., "Comparison of 11 phenotypic assays for accurate detection of carbapenemase-producing Enterobacteriaceae," Journal of Clinical Microbiology, Apr. 1, 2017, 55(4):1046-55.

Thomson et al., "CPO Complete, a novel test for fast, accurate phenotypic detection and classification of carbapenemases," PloS one, Dec. 11, 2019, 14(12), 13 pages.

Tijet et al., "Detection of carbapenemase activity in Enterobacteriaceae: comparison of the carbapenem inactivation method versus the Carba NP test," Journal of Antimicrobial Chemotherapy, Jan. 1, 2016, 71(1):274-6.

EP Extended European Search Report in European Appln. No. 18845539.8, dated Jun. 24, 2020, 6 pages.

\* cited by examiner

METHODS AND KITS FOR DETECTING ANTIBIOTIC-INACTIVATING FACTORS

CROSS REFERENCE TO RELATED APPLICATIONS

This application is a U.S. national phase filing under 35 U.S.C. § 371 of International Application No. PCT/US2018/046775 titled "METHODS AND KITS FOR DETECTING ANTIBIOTIC-INACTIVATING FACTORS", filed Aug. 14, 2018, which claims benefit under 35 U.S.C. 119(e) to U.S. Application No. 62/545,239 filed Aug. 14, 2017 and U.S. Application No. 62/657,429 filed Apr. 13, 2018. The disclosures of these applications are incorporated by reference in their entirety.

TECHNICAL FIELD

The presently-disclosed subject matter generally relates to methods and kits for detecting antibiotic-inactivating factors. In particular, certain embodiments of the presently-disclosed subject matter relate to methods and kits for detecting antibiotic-inactivating factors that make use of permeabilizing or cell lysis agents, substrates for antimicrobial-inactivating factors, and indicators to detect antimicrobial-inactivating activity.

BACKGROUND

Clinicians and veterinarians often utilize laboratory tests to select optimal antimicrobial therapies for infections. The most commonly used type of laboratory test for this purpose is the antibiotic susceptibility test. Antibiotic susceptibility tests determine the in vitro inhibitory activity of antibiotics against microorganisms that cause infections. If the test indicates that an antibiotic is sufficiently potent to treat an infection, the microorganism causing the infection is reported to be "susceptible" to the antibiotic. If the antibiotic lacks sufficient potency for successful therapy, the microorganism is reported as "resistant" to the antibiotic. In some tests, other susceptibility categories may be reported e.g. "moderate susceptibility", "intermediate susceptibility", or "susceptible dose dependent".

A failure of currently available antibiotic susceptibility tests is their failure to reliably predict the outcome of therapy or to detect the occurrence of important resistance mechanisms in microorganisms. Sometimes an antibiotic will fail to cure an infection even though the microorganism is susceptible to the antibiotic in the laboratory test. That is, the current routine laboratory tests can be misleading and give an over-optimistic impression of the therapeutic potential of antibiotics. These tests can cause patients to be given ineffective treatments. In serious infections, this inadequacy of current tests can have fatal consequences. To protect patients from the adverse consequences that may arise from the failure of antibiotic susceptibility tests, laboratories may also perform tests to detect antibiotic resistance mechanisms.

There are many reasons for failures of antibiotic therapies that were initiated on the basis of antibiotic susceptibility tests. Some involve patient-related factors. Some involve pathogen-related factors. However, one explanation is error arising from a deficiency in the antibiotic susceptibility test itself. That deficiency is that current routine susceptibility tests do not detect the antibiotic-inactivating potential of some microorganisms. Some microorganisms produce antibiotic-inactivating factors (typically enzymes) that inactivate antibiotics. The best known enzymes of this type are the beta-lactamases that certain bacteria produce to inactivate beta-lactam antibiotics. Such enzymes, which are not detected in routine antibiotic susceptibility tests, may cause sufficient antibiotic inactivation at the site of an infection in a patient to cause treatment failure.

The principal beta-lactamases known to cause therapeutic failures that are not reliably predicted by antibiotic susceptibility tests are extended spectrum beta-lactamases (ESBLs), plasmid-mediated AmpC beta-lactamases, and carbapenemases (1). Each of these beta-lactamase types is of high clinical concern because the genes encoding them are typically associated with other antibiotic resistance genes, leaving few therapeutic options. The pathogens of greatest current concern are gram-negative bacteria that produce carbapenemases. Carbapenemase-producing pathogens are associated with high mortality and because there may be few of no effective antibiotics for therapy. The most reliable treatment of infections by carbapenemase-producing pathogens requires treatment with a combination of two or more antibiotics to which the pathogen is susceptible. Treatment with a single antibiotic to which the pathogen is susceptible is associated with high mortality comparable to when patients are treated with an antibiotic to which the pathogen is resistant (2, 3). It is therefore of life-saving importance for laboratories to detect carbapenemase production by pathogens so as to alert clinicians to the need to use combination therapy.

In other words, there is a need to provide clinicians with information about both the antimicrobial activity of antimicrobial agents such as antibiotics and also the ability of microorganisms to inactivate antimicrobial agents. Such tests should improve the quality of therapeutic decision-making by clinicians when selecting antibiotic therapies for patients with infections.

Antibiotic susceptibilities are determined routinely by disk diffusion or antibiotic dilution methods, or by methods derived from these two methods, some of which involve automated instruments such as the Vitek 2 (bioMérieux, Inc. Durham, N.C.), MicroScan Walkaway (Beckman Coulter, Sacramento, Calif.) and BD Phoenix (BD Diagnostics, Sparks, Md., 21152). All of these methods are generally deficient in that they do not yield information about the ability of antibiotic-inactivating factors of microorganisms to inactivate antibiotics. Various techniques for detecting antibiotic-inactivating enzymes of microorganisms have been reported in the scientific literature. Some are used to detect the activity of specific antibiotic-inactivating enzymes (e.g. beta-lactamases), while others are non-specific and detect enzymes that inactivate more than one class of antibiotics. The following are exemplary tests used to detect antibiotic-inactivating enzymes of bacteria.

There are specific tests for the detection of chloramphenicol acetyl-transferase (4). These are complex tests to detect enzymatic inactivation of chloramphenicol and require special instruments capable of measuring the absorbance of light at specific wavelengths. Such tests are not antibiotic susceptibility tests and their complexity is such that they are unsuitable for routine clinical microbiology laboratories.

The production of beta-lactamases by *Staphylococcus aureus* is inferred by the production of a distinctive heaped-up inhibition zone margin around a penicillin antibiotic disk (5). beta-lactamase production by many types of bacteria can also be detected chemically by testing the bacteria with an indicator substance such as nitrocefin (6, 7). These tests are reliable indicators only of beta-lactamase-mediated resistance of *Staphylococcus aureus, Staphylococcus epider-* midis, *Moraxella catarrhalis, Neisseria* and *Haemophilus* species to certain types of penicillin antibiotics. They do not predict the potential for any other bacteria to resist these penicillins, and they do not predict the potential for any bacteria to be resistant to any other class of beta-lactam antibiotics, such as cephalosporins, cephamycins, monobactams, monocarbams, penems or carbapenems. In short, these are useful tests of limited scope and more comprehensive testing is needed to detect the activities of other types of beta-lactamases or of all beta-lactamases against all beta-lactam antibiotics.

Disk diffusion tests can be modified by a pre-incubation procedure to determine the ability of beta-lactamases from *Staphylococcus aureus* to inactivate beta-lactam antibiotics (8). This procedure results in smaller inhibition zones than those for which the interpretive criteria of the tests were calibrated. The pre-incubation procedure thereby invalidates the interpretive tables that are necessary to determine antibiotic susceptibility or resistance. This is a serious deficiency as it would be unethical to base therapy on this procedure which lacks validated interpretive criteria. There are various other types of beta-lactamase detection tests based on disk diffusion test methodologies. They require overnight incubation, which is a disadvantage because it may delay the availability of results by an additional day. They can also be inconvenient because they usually involve additional procedures for the lab to perform.

Gots' test (9), also known as the Clover Leaf test (10, 11), the Hodge test (12), and the Modified Hodge test (13), is used to detect beta-lactamases and also claims to detect two other types of antibiotic inactivating enzymes, chloramphenicol acetyltransferase and erythromycin esterase. This test is not an antibiotic susceptibility test and must be set up as an additional procedure. In addition to this inconvenience, there are doubts about its accuracy (14-16).

The cefoxitin induction test (17) is a special test for detecting a particular type of beta-lactamase, the inducible AmpC beta-lactamase of Bush Group 1 (18, 19). This test is of limited utility as does not detect all types of beta-lactamases. It is used to supplement antibiotic susceptibility tests and is not, in itself, an antibiotic susceptibility test.

The double disk potentiation test is used to determine if a strain of Enterobacteriaceae produces an ESBL (20). It involves strategically placing an amoxicillin/clavulanate disk 20 to 30 mm from disks containing cefotaxime, ceftriaxone, ceftazidime, ceftizoxime or aztreonam on an agar plate. This test is based on the ability of the beta-lactamase inhibitor, clavulanate, to inhibit the ESBL and prevent it from inactivating the cephalosporin or aztreonam antibiotics in the test. It is usually a special additional procedure for detection of a particular beta-lactamase, not a routine antibiotic susceptibility test, and is inconvenient and limited in scope. Some laboratories include this test, or derivatives of it, in the routine antibiotic susceptibility test. This is a convenient approach, but its inclusion in the susceptibility test usually requires the omission of other antibiotics from the susceptibility test, which is a disadvantage.

A variety of disk and dilution tests have been derived from the principle of the double disk test (21-27). That is, they use the ability of a beta-lactamase inhibitor to inhibit an extended spectrum beta-lactamase to detect this type of beta-lactamase.

The 3-dimensional test (28, 29) is, in its direct form, a modification of the disk diffusion test that simultaneously yields information about both the antibiotic susceptibility and the ability of a microorganism to inactivate beta-lactam antibiotics. After the agar is inoculated with a lawn of the test microorganism, a sterile scalpel is used to cut a slit in the agar 3 mm from where the disks are to be placed on the inoculated agar surface. A dense liquid inoculum of the test organism (the 3-dimensional inoculum) is then dispensed into the slit, the antibiotic disks are placed on the agar 3 mm from the slit, and incubated.

After incubation, the inhibition zones are measured by standard procedures to determine the susceptibility or resistance of the microorganism to the test antibiotics according to the interpretive criteria of the disk diffusion test. In addition to this, enzymatic inactivation of the antibiotics can be detected by inspecting the intersections of the 3-dimensional inoculum and the margins of the inhibition zones. Antibiotic inactivation results in a distortion or discontinuity in the usually circular inhibition zone. The 3-dimensional test thus allows the laboratory to report to the clinician not only the susceptibility or resistance of a microorganism to antibiotics, but also the ability of the microorganism to inactivate the antibiotics. There are several problems, however, with this test. Making a slit in the agar is technically difficult and inconvenient, and it is difficult to accurately deliver the inoculum into the slit without overfilling the slit and possibly invalidating the test.

The AmpC Disk test (30) was designed to detect AmpC beta-lactamases and adaptations of this test have been used to detect other beta-lactamases (see, e.g., U.S. Pat. Nos. 7,166,442 and 7,807,403). The principle of the test utilizes bifunctional disks impregnated with Tris/EDTA. Tris/EDTA acts as a permeabilizing agent to disrupt bacterial membranes, causing a loss of cell contents. It is also a chelating agent, which inhibits the activity of class B carbapenemases (metallo-beta-lactamases or MBLs). In the indirect form of testing with Tris/EDTA disks, the surface of an agar plate is inoculated with a fully susceptible assay strain such as *E. coli* ATCC 25922 and a substrate disk is placed on the agar surface. A Tris/EDTA disk which has been heavily inoculated with the test strain is then placed 1 mm from a substrate disk with the inoculated side of the Tris/EDTA disk placed in contact with the agar. The plate is then incubated overnight and is examined for an indentation or a flattening of the zone of inhibition in the vicinity of the substrate disk. An indentation or flattening is a positive test result, which indicates enzymatic inactivation of the substrate. A variety of substrates can be used to detect different types of beta-lactamases for detection, e.g., cefoxitin is a substrate for detection of AmpC beta-lactamases and carbapenems are substrates for the detection of carbapenemases.

As mentioned above, the most critical current need is for a rapid, convenient and accurate test to detect carbapenemase-producing pathogens. Clinical laboratories currently use a variety of carbapenemase detection tests but all are suboptimal with respect to speed, convenience or accuracy or a combination of these factors, or are too expensive for routine use. Moreover, none of the methods can be performed using an automated microbiological analyzer.

The following are exemplary tests currently used to detect carbapenemases produced by bacteria. They are described in three groups, 1) phenotypic tests requiring overnight incubation; 2) rapid phenotypic tests (typically requiring less than five hours test time); and 3) molecular tests.

Phenotypic Tests Requiring Overnight Incubation

The Modified Hodge test (Gots' test) is used as a confirmatory test for carbapenemase production (31). It is cheap and convenient, but does not reliably distinguish between carbapenemases and hyperproduced AmpC beta-lactamases, does not reliably detect metallo-beta-lactamases, and can be difficult to interpret (16). Therefore, it is deficient in sensitivity and specificity. In addition, it does not distinguish between the three molecular classes of carbapenemases, Classes A, B, and D. The inability to identify the molecular class of a carbapenemase is of therapeutic importance. Knowledge of the molecular class of a carbapenemase can guide a clinician in the choice of appropriate antibiotic therapy. In short, this test is suboptimal because it has poor accuracy, cannot distinguish between carbapenemase classes, and is not sufficiently rapid.

As mentioned above, the AmpC Disk test can be adapted for carbapenemase detection through utilizing a carbapenem as substrate and can differentiate between carbapenemases of molecular classes A, B and D (32, 33). The differentiation between carbapenemase types is achieved because class B carbapenemases (metallo-beta-lactamases) are inhibited by chelating agents such as EDTA, mercaptopropionic acid, and dipicolinic acid. The EDTA in the disk is seen to inhibit metallo-beta-lactamases when a second Tris/EDTA disk is strategically placed in the vicinity of a carbapenem disk (typically 5 to 10 mm away) as a source of EDTA to protect the carbapenem from inactivation if the microorganism is a metallo-beta-lactamase-producer (33). A positive test for a metallo-beta-lactamase-production shows as an extension of the zone of inhibition in the vicinity of the carbapenem disk or as a lens of inhibition between the two disks. This indicates the EDTA has inhibited the organism's metallo-beta-lactamase, thereby restoring activity to the carbapenem.

Microorganisms that produce Class A or D carbapenemases are detected by an indentation or flattening of the zone of inhibition in the vicinity of the inoculated Tris/EDTA disk that is located typically 1 mm from the carbapenem disk. The distinction between Class A and D carbapenemases can be achieved through placement of an additional Tris/EDTA disk supplemented with boronic acid and inoculated heavily with the test microorganism and placed approximately 1 mm from the carbapenem disk on the opposite side from the disk that was not supplemented with boronic acid. Boronic acid selectively inhibits Class A carbapenemases (34) but not Class D carbapenemases. If an isolate produces a Class A carbapenemase, the boronic acid prevents the formation of an indentation or flattening of the margin of the inhibition zone. If the boronic acid does not prevent the formation of an indentation or flattening of the margin of the inhibition zone, the carbapenemase belongs to molecular Class D.

Thus, tests with Tris/EDTA disks can conveniently and inexpensively detect and differentiate carbapenemases of Classes A, B and D. The disadvantages of this test are that occasionally falsely positive results occur due to high levels of AmpC production and also this is an overnight test, and therefore, not sufficiently rapid.

The Rosco Neo-Sensitabs KPC+MBL Confirm ID kit (ROSCO Diagnostica A/S, Taastrup, Denmark) is based on four Tablets, each of which contain the carbapenem, meropenem, and three of which also contain a beta-lactamase inhibitor. Tablet A contains meropenem, Tablet B contains meropenem and the metallo-beta-lactamase inhibitor, dipicolinic acid, Tablet C contains meropenem and cloxacillin (AmpC inhibitor), and Tablet D contains meropenem and boronic acid (inhibitor of AmpC and class A carbapenemases). A positive test occurs when an inhibitor causes a 5 mm larger zone size than meropenem alone. A positive test with Tablet B is interpreted as detection of class B carbapenemase activity; a positive test with Tablet D is interpreted as detection of class A carbapenemase activity; if Tablets C and D both yield positive tests, the interpretation is detection of AmpC activity coupled with porin loss (impermeability). This test has been reported to lack sufficient sensitivity and specificity for reliable detection of class A and B carbapenemases (16).

Mastdiscs ID inhibitor combination disks (Mast Diagnostics, Bootle, UK) is a four disk test that is comparable to the Rosco Neo-Sensitabs KPC+MBL Confirm ID kit and has been similarly reported to lack sufficient sensitivity and specificity for reliable detection of class A and B carbapenemases (16).

The Carbapenem Inactivation Method (CIM) consists of incubation of a meropenem disk with the test isolate followed by placing the disk on a lawn culture inoculated with *Escherichia coli* ATCC 25922. The absence of an inhibition zone after extended incubation, typically overnight, indicates enzymatic hydrolysis of meropenem during the first incubation step, whereas an inhibition zone appears if the tested isolate does not express carbapenemase activity (van der Zwaluw et al.) This test is accurate, cheap and convenient, but requires at least 8 hours (typically overnight) incubation before the results may be read. It also lacks the ability to discriminate between the molecular classes of carbapenemases (35).

The metallo-beta-lactamase (MBL) Etest (bioMérieux, Inc. Durham, N.C.) is a specific test to detect metallo-beta-lactamases. It generates an antibiotic concentration gradient in agar to facilitate the comparison of MICs obtained when a carbapenem is tested alone and tested in combination with EDTA. The test is positive if EDTA is associated with a decrease of at least 8-fold in the carbapenem MIC. This Etest can be difficult to interpret because MICs of imipenem (the substrate most commonly used) in the test are often low, off-scale, and uninterpretable in tests with Enterobacteriaceae. If meropenem is used as the substrate, tests with *Pseudomonas aeruginosa* can yield falsely negative for isolates that have upregulated efflux as a resistance mechanism. This test is specific for class B carbapenemases only, and is therefore of limited scope in addition to its accuracy issues and the need for overnight incubation Rapid Phenotypic Tests The Carba NP test is a rapid phenotypic carbapenemase detection test (36) (see WO 2012175637). This test is accurate for detection of most carbapenemases. A preparation step is necessary prior to assaying for carbapenemase activity. This step comprises the harvesting of the test strain from an appropriate culture medium by using a 10 μL calibrated loop (37). Either of two alternative steps may then be used. These are a) resuspending the test strain in B-PERII lysis buffer, followed by a vortexing step and a 30-minute incubation step after which the resultant lysate is centrifuged for 5 minutes to provide the supernatant that is used in the test (38), orb) the lysis step is simplified by using a smaller inoculum comprising only ¼ to ⅓ of a 10 μL calibrated loop which is resuspended in 100 μL of PERII lysis buffer and used in the test without subsequent vortexing, incubation, or centrifugation (37).

After the test organism is lysed to release its beta-lactamases, 30 μL of the enzyme preparation is then mixed in a 96-well tray with 100 μL of a 1-mL solution comprising 3 mg of imipenem monohydrate, phenol red solution, and 0.1 mmol/L zinc sulfate. The phenol red solution is prepared by mixing 2 mL of a phenol red solution 0.5% (wt/vol) with 16.6 mL of distilled water and the pH adjusted to 7.8 by adding drops of 1 N NaOH. The test is then incubated at 37° C. for up to 2 hours. A positive test is indicated by a color change from red to yellow or orange. This corresponds to the hydrolysis of imipenem to produce acid. A parallel test without the addition of imipenem (the test control) is also necessary to ensure that the enzyme preparation itself does not lower the pH sufficiently to produce a falsely positive result. In some tests, comparison of the test and the test control wells is required to aid test interpretation for strains that produce results that are difficult to interpret.

Several aspects of the test are problematic. Enzyme preparation involves harvesting bacteria into lysis buffer, vortexing, incubation for 30 minutes, centrifugation for 5 minutes, and decanting the supernatant. This is time consuming, especially when multiple bacterial isolates are tested because each isolate must be harvested, placed into an appropriate tube that must be labeled, vortexed, added to the centrifuge and removed, and decanted individually into an appropriate tube that must be labeled. Also, the 10 µL loop used for harvesting bacteria is bulky to work with and may necessitate having a greater amount of bacteria available for the test than may be present on a culture plate. A falsely negative result may be obtained if insufficient bacterial cells are used for the test or the test may have to be delayed until there is sufficient bacterial growth for the test. A delayed rapid test is not a rapid test. This potential disadvantage arises in part because of the volumes required for the test (30 µL of enzyme preparation and 100 µL of test solution for both the test and the test control). The preparation of the reaction solution involves the weighing of chemicals, the adjustment of pH by the addition of NaOH. These are procedures that are usually performed in chemistry laboratories, not microbiology laboratories, and are mostly unfamiliar to microbiologists. Consequently, the laboratory may be required to purchase chemicals and a pH meter, and staff may be slow or inaccurate in the performance of these procedures. A further problem is that imipenem monohydrate is expensive in some countries (e.g. $317.00 USD for 100 mg, Sigma-Aldrich, St Louis, Mo., cat no. 1337809) and very unstable, necessitating fresh preparation of the imipenem-containing solution at least every three days.

For these reasons, the test is not convenient for routine clinical microbiology laboratories and is more suited to research laboratories. There have been criticisms of the accuracy of the test in detection of OXA-48-like carbapenemases of Class D and also for the detection of GES and NDM carbapenemases (35, 39, 40).

There are marketed adaptations of the Carba NP test, which suggest that there may be weaknesses in its application. For example, the Rosco Neo-RapidCARB Kit (ROSCO Diagnostica A/S, Taastrup, Denmark) was the first commercial adaptation of the Carba NP test. It uses reagent tablets that have 2 years stability, compared to the 3 days stability of solution A for the Carba NP test. It is based on the same principles as the Carba NP test and tests can be read within two hours. As with the Carba NP test, this test also requires the addition of a test control for each test isolate. Tests with some bacterial strains are difficult to interpret (41, 42), but modifications to the recommended procedure can enhance comparisons between the colors of the test and test control tubes to improve sensitivity and confer a level of convenience that is suitable for clinical laboratories (43). Specificity problems, i.e., falsely positive results, due to bacteria producing non-carbapenemase beta-lactamases such as AmpCs or ESBLs have been reported (41). This test must be followed by appropriate molecular testing to identify the molecular class of carbapenemase detected.

The Rapidec Carba NP test (bioMérieux, Inc. Durham, N.C.) is a new commercially available derivative of the Carba NP test aimed at overcoming the imipenem instability problem of the original Carba NP test. It contains a number of wells for reconstituting reagents and preparing the inoculum. As with the other rapid phenotypic tests, the test is read by comparing the colors of the test and test control wells. The test is positive if there is a significant variation in color between the two wells. Early evaluations report it to be accurate for detection of most carbapenemases and suitable for clinical laboratories, but liable to yield falsely negative results with some bacteria producing OXA-48, OXA-48-like, and IMP carbapenemases and falsely positive results with some carbapenem-resistant, carbapenemase-negative *E. coli* and *P. aeruginosa* isolates (44-46). In addition, this test must be followed by appropriate molecular testing to identify the molecular class of carbapenemase detected.

The Blue-Carba test (47) is a modification of the Carba NP test but uses a different pH indicator, bromothymol blue instead of phenol red and tests colonies rather than bacterial extracts. Like the Carba NP test, imipenem is included in the test but whether or not it is included as a substrate for carbapenemases is uncertain. The test was initially reported to detect carbapenemases from their intrinsic pH values and not from the production of acid as a consequence of hydrolysis of imipenem (47). An alternative explanation of the principle of the test is that hydrolysis of imipenem is detected (48). The test has been reported to be accurate for detection of class A carbapenemases and metallo-beta-lactamases but lacks sensitivity for detection of class D OXA-48-like carbapenemases (49). Rosco (ROSCO Diagnostica A/S, Taastrup, Denmark) markets a version of this test, the Rosco Rapid Carb Blue test, which was reported to have high accuracy but failed to detect some GES and OXA carbapenemases (50, 48). This test also must be followed by appropriate molecular testing to identify the molecular class of carbapenemase detected.

Molecular Tests

Polymerase chain reaction (PCR), microarray and DNA sequencing approaches to carbapenemase detection have considerable potential for rapid detection of carbapenemases produced by microorganisms cultured from clinical specimens and also for direct detection from clinical specimens. For most laboratories, these advantages are offset by the high cost and technical complexity of the tests. There are also some accuracy problems. Molecular tests focus on specific resistance mechanisms and, in PCR tests, it is possible to focus only on detection of single or small numbers of genes encoding resistance mechanisms. This can leave important diagnostic gaps that are not covered and lead to falsely negative results. In addition, there is the potential for false positive results. This can occur with tests to detect genes encoding OXA-48-like and GES carbapenemases because the molecular tests detect genes encoding both carbapenemases and non-carbapenemases (51). False positive results also can occur if the tests detect genes which are either not expressed or do not confer resistance.

Microarray tests are more comprehensive than PCR tests and can detect a more extensive range of antibiotic resistance genes. These tests are more expensive than PCR tests, are used mainly by reference laboratories, and are not currently suitable for widespread use in routine clinical laboratories.

In short, although molecular tests offer considerable potential for rapid, accurate and highly specific detection of antibiotic resistance mechanisms, their routine employment awaits resolution of issues such as cost, convenience, and accuracy, while phenotypic tests cast a broader diagnostic net and are capable of detecting resistance mechanisms not included in the target ranges of molecular tests.

SUMMARY

The presently-disclosed subject matter includes methods of detecting the presence of antibiotic-inactivating enzymes. In some implementations, a culture of the microorganism to be investigated is first admixed with a solution containing a substrate antimicrobial agent for the enzyme and a permeabilizing or lysis agent for the microorganism. In some embodiments, additional components of the solution could be an antibiotic-inactivating enzyme activator, an indicator to detect antibiotic-inactivating activity and one or more enzyme inhibitors to selectively inhibit antibiotic-inactivating enzymes and thereby differentiate between different types of antibiotic inactivating enzymes. In some implementations, the assay mixture is then incubated under appropriate conditions for a time suitable to determine if inactivation of the substrate antibiotic has occurred.

In one aspect, methods for rapidly detecting whether or not a microorganism produces a beta-lactamase (sometimes referred to as an antibiotic-inactivating factor or an antimicrobial-inactivating factor) are provided. Such a method typically includes incubating an admixture for a period of time under appropriate conditions, the admixture comprising the microorganism, a permeabilizing or lysis agent, a beta-lactam antibiotic (sometimes referred to as a substrate for an antibiotic-inactivating factor), and an indicator (e.g., an indicator of antimicrobial-inactivating activity); and determining the presence, absence and/or status of the indicator, thereby determining whether or not the microorganism produces a beta-lactamase.

In some embodiments, the beta-lactamase is a carbapenemase. In some embodiments, the microorganism is selected from the group consisting of members of the family Enterobacteriaceae, *Pseudomonas seudomonas* spp., *Acinetobacter* spp., *Stenotrophomonas maltophilia*, *Bacteroides* spp., *Bacillus cereus*, and *Aeromonas* spp.

Representative permeabilizing or lysis agents include, without limitation, inorganic salts, quaternary ammonium compounds, buffer solutions, hypotonic or hypertonic agents, antibiotics, detergents or surfactant-containing agents, CHAPS electrophoresis reagent, lactic acid, sodium hexametaphosphate, natural peptide agents such as cecropins, bactenecin, tachyplesins and synthetic peptides, B-PER, B-PER II, and the proteolytic enzyme, achromopeptidase, and polymyxin B. Representative beta-lactam antibiotics (sometimes referred to as a substrates for the antibiotic-inactivating factor) include, without limitation, imipenem, doripenem, meropenem, ertapenem, biapenem, faropenem, lenapenem, razupenem, thienamycin, tebipenem, tomopenem, panipenem, or a combination thereof. Representative indicators include, without limitation, phenol red, bromothymol blue, neutral red, naphtholphthalien, and cresol red.

In some embodiments, the admixture can further include one or more beta-lactamase inhibitors (e.g., inhibitors for selectively inhibiting an antimicrobial inactivating enzyme). In some embodiments, the one or more inhibitors includes an inhibitor of Class A beta-lactamases (e.g., boronic acid, boric acid, clavulanate, avibactam, sulbactam, vaborbactam, or tazobactam). In some embodiments, the one or more inhibitors includes an inhibitor of Class B beta-lactamases (e.g., EDTA, dipicolinic acid, clavulanate, avibactam, sulbactam, vaborbactam, tazobactam, a phenazine, a biphenyl tetrazole, a pyridine dicarboxylate, a sulphonyl-triazole, a succinic acid derivative, a 1beta-methylcarbapenem, a mercaptophosphonate compound, a mercaptoacetic acid thiol ester, mercaptoacetic acid, thiomandelic acid, 1,2-benzenedimethanethiol, a trifluoromethyl ketone or a trifluoromethyl alcohol). In some embodiments, the one or more inhibitors includes an inhibitor of Class C beta-lactamases (e.g., boric acid, cloxacillin, flucloxacillin, dicloxacillin, nafcillin, oxacillin, methicillin, boronic acid, clavulanate, avibactam, sulbactam, vaborbactam, tazobactam, aztreonam, or vaborbactam). In some embodiments, the one or more inhibitors includes an inhibitor of Class D beta-lactamases (e.g., sodium chloride or avibactam).

In some embodiments, the admixture further includes an activator of a beta-lactamase (e.g., zinc sulfate). In some embodiments, the admixture further includes glucose and/or thimerosal (also known as thiomersal).

In another aspect, a kit for detecting beta-lactamases is provided. Such a kit can include a permeabilizing or cell lysis agent; a beta-lactam antibiotic, and an indicator for detecting antibiotic-inactivating activity.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Like reference symbols in the various drawings indicate like elements.

DETAILED DESCRIPTION

Figure 1:
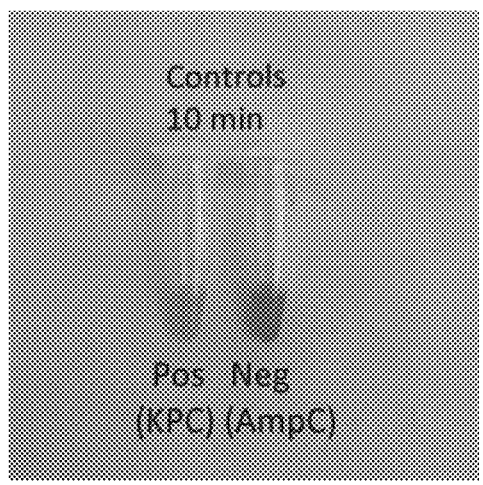
FIG. 1. Representative positive and negative tests using positive control isolate *Klebsiella pneumoniae* BAA 1705 and negative control isolate *Klebsiella aerogenes* (formerly known as *Enterobacter aerogenes*) G1614.

The presently-disclosed subject matter is based, at least in part, on the discovery of a novel and extremely rapid method for detecting whether or not microorganisms produce beta-lactamases (sometimes referred to herein as antibiotic-inactivating factors or antimicrobial-inactivating factors). It is based upon disrupting the permeability barriers of a microorganism (e.g., outer membrane, cell membrane, or cell wall) by incubating the microorganism in the presence of a permeabilizing or cell lysis agent, a beta-lactam antibiotic (i.e., the substrate of the beta-lactamase), and an indicator. In some instances, it is useful to identify the particular class of beta-lactamase; in these instances, one or more inhibitors can be included in the admixture to selectively inhibit certain types or classes of beta-lactamases, along with any activators of beta-lactamases, if desired.

As described herein, there are several classes of beta-lactamases that can be detected by the methods described herein. While the methods described herein were exemplified using the carbapenemase class of beta-lactamases, the methods described herein also can be used to detect other classes of beta-lactamases such as extended spectrum beta-lactamases (ESBL) and plasmid-mediated AmpC beta-lactamases. As such, the methods described herein are independent of the microorganism producing the beta-lactamase and can be used, for example, to determine whether or not a member of the family Enterobacteriaceae, a *Pseudomonas* spp., an *Acinetobacter* spp., an *Aeromonas* spp., a *Bacteroides* spp., a *Bacillus cereus* microorganism or a *Stenotrophomonas maltophilia* microorganism produces a beta-lactamase.

The microorganism to be evaluated for production of a beta-lactamase can be obtained from any number of sources. For example, one or more microorganisms can be in liquid culture media (e.g., enrichment broths, susceptibility test broths, general growth broths), liquid clinical samples (e.g., urine, cerebrospinal fluid, blood, exudates (e.g. transudate, ulcer), peritoneal fluid, pleural fluid, suprapubic aspirate, abscess, pus); and/or tissue samples (e.g., biopsies), which can be tested directly or inoculated into liquid growth media.

Permeabilizing or lysis agents are known and used routinely in the art. Representative permeabilizing or lysis agents include, without limitation, inorganic salts, quaternary ammonium compounds, buffer solutions, hypotonic or hypertonic agents, antibiotics, detergents or surfactant-containing agents, CHAPS electrophoresis reagent, lactic acid, sodium hexametaphosphate, natural peptide agents such as cecropins, bactenecin, tachyplesins and synthetic peptides, B-PER, B-PER II, and the proteolytic enzyme, achromopeptidase, and polymyxin B.

The beta-lactam antibiotic that is used in the admixture can be any beta-lactam antibiotic and will be dependent upon which antibiotic is being considered for treatment of a particular infection. Representative beta-lactam antibiotics include, without limitation, imipenem, doripenem, meropenem, ertapenem, faropenem, lenapenem, razupenem, thienamycin, tebipenem, tomopenem, panipenem, and biapenem. It would be appreciated that multiple admixtures can be generated, each containing a different beta-lactam, or a combination of one or more beta-lactams can be used in an admixture.

Indicators also are known in the art and typically are based upon a change in pH (e.g., a change in hydronium ions (H3O+) or hydrogen ions (H+) in a solution, which occurs with the hydrolytic cleavage of the beta-lactam ring of the antibiotic. Exemplary pH indicators that can be used in the methods described herein include, without limitation, phenol red, bromothymol blue, neutral red, naphtholphthalien, and cresol red. The indicators suitable for use in the methods described herein are not limited to pH indicators; any type of indicator that detects the inactivation of the beta-lactam via hydrolysis or another mechanism can be used in the methods described herein.

In some instances, it may be desirable to include an activator or enhancer of beta-lactamase activity in the admixture. Activators or enhances of beta-lactamases are known in the art and include, for example, zinc sulfate.

In some instances, it may be desirable to add glucose and/or thimerosal (also known as thiomersal) to the admixture. In some embodiments, glucose can be added to a final concentration of about 0.1 mg/ml to about 10 mg/ml (e.g., about 0.5 mg/ml to about 7.5 mg/ml; about 1 mg/ml to about 5 mg/ml; about 2.5 mg/ml to about 6 mg/ml) and thimerosal can be added to a final concentration of about 4.3 mg/ml to about 17 mg/ml (e.g., about 5 mg/ml to about 15 mg/ml; about 7.5 mg/ml to about 12.5 mg/ml; about 8 mg/ml to about 10 mg/ml). While the exact mechanisms of action of the glucose or the thimerosal in the admixture are not fully understood, and while neither is essential, appear to contribute to the rapidness of the methods described herein.

As indicated herein, there may be circumstances in which it is useful to identify the class of beta-lactamase that is being produced by a particular microorganism. Under these circumstances, one or more inhibitors (e.g., selective inhibitors) of a class of beta-lactamases can be included in the admixture and the presence or the absence of the indicator can be determined.

While not intending to be exhaustive, representative inhibitors of Class A beta-lactamases include boronic acid, boric acid, clavulanate, avibactam, sulbactam, vaborbactam, and tazobactam; representative inhibitors of Class B beta-lactamases include EDTA, dipicolinic acid, a phenazine, a biphenyl tetrazole, a pyridine dicarboxylate, a sulphonyltriazole, a succinic acid derivative, a 1beta-methylcarbapenem, a mercaptophosphonate compound, a mercaptoacetic acid thiol ester, mercaptoacetic acid, thiomandelic acid, 1,2-benzenedimethanethiol, a trifluoromethyl ketone, a trifluoromethyl alcohol, clavulanate, avibactam, sulbactam, vaborbactam, and tazobactam; representative inhibitors of Class C beta-lactamases include boric acid, cloxacillin, flucloxacillin, dicloxacillin, nafcillin, oxacillin, methicillin, boronic acid, clavulanate, avibactam, sulbactam, tazobactam, aztreonam, and vaborbactam; and representative inhibitors of Class D beta-lactamases include sodium chloride and avibactam. It would be understood that a suitable amount of a beta-lactamase inhibitor is an amount that inhibits most or all (e.g., at least 80%, at least 85%, at least 90%, at least 95%, at least 99%, at least 100%) of the beta-lactamase activity while not disrupting or causing toxicity to the other components in the admixture or to the admixture itself.

Any of the components of the admixture as described herein can be packaged appropriately and provided in a kit for use in detecting whether or not a microorganism produces a beta-lactamase. Kits, also known as articles of manufacture, are known in the art, as are packaging materials for such kits.

DESCRIPTION OF EXEMPLARY EMBODIMENTS

In some implementations, in assaying a microorganism for its ability to make or excrete a beta-lactamase, control assays can also be prepared under similar conditions using microorganisms known to either produce or not produce the beta-lactamase(s) that is/are the target of the assay.

In some implementations, the methods of the presently-disclosed subject matter are designed to increase the amount of information provided about the interaction of microorganisms with antibiotics. In some implementations, the methods provide a means to rapidly detect the ability of microorganisms to inactivate antibiotics. This information can be useful in selecting appropriate antibiotic therapies for the treatment of infections, in providing epidemiological information about the microorganisms, in antibiotic research, and in other fields of biological research such as genetics and enzymology.

In some implementations, the methods of the presently-disclosed subject matter comprise the step of providing a tube containing a test solution comprising one or more chemicals that will facilitate the release of beta-lactamases from bacteria or other microorganisms, an antibiotic which the beta-lactamases are capable of inactivating, an activator of the beta-lactamases, an inhibitor of Class C (AmpC) beta-lactamases, and an indicator. In some implementations, these ingredients are provided in liquid form as a solution or as a lyophilized deposit which must be reconstituted prior to testing by the addition of an appropriate liquid, such as sterile water or culture media In some implementations wherein the methods of the presently-disclosed subject matter are used to detect the production of one or more carbapenemases by a microorganism, a suitable stock of the test solution for testing multiple microorganisms is made using the following amounts of components in the form described herein below: 800 µl of cloxacillin solution, 140 µl of B-PER II, 140 µl of phenol red and 25 µl of 10 mM zinc sulfate solution. Inoculum for the test comprises colonies on a culture plate harvested with a 1 µl bacteriological loop and admixed in the test solution by inserting and twirling the loop in 25 µl of the test solution in a 0.2 ml clear PCR tube. The harvesting and admixing step is repeated to increase the inoculum of microorganisms in the test. The tube is then capped and incubated at a temperature between 25° C. and 37° C. and inspected after approximately 5 minutes for a color change from red (negative) to yellow or orange (positive). If the test is negative, it is re-inspected after incubation for approximately 30 minutes. If negative this process is repeated with inspections as needed at approximately 1 hour and 2 hours.

In some implementations of the methods for detecting carbapenemases, pharmaceutical grade imipenem/cilastatin is used as the substrate rather than pure imipenem monohydrate. In other implementations, the method is conducted in triplicate with the additional two tests supplemented with boronic acid and EDTA, respectively, to determine the molecular class of a carbapenemase. The unsupplemented test detects the presence or absence of carbapenemase activity. Class A carbapenemases are detected if the unsupplemented test is positive and the boronic acid-supplemented test is negative; Class B (i.e. metallo-beta-lactamase) carbapenemases are detected the unsupplemented test is positive and the EDTA-supplemented test is negative; and Class D carbapenemases are detected if all three tests are positive.

It should be understood that while a certain embodiments of the presently-disclosed subject matter are as described above, the presently-disclosed subject matter is not limited to that embodiment. Other tubes, vessels or carriers of reagents, such as filter papers, pieces of nitrocellulose or other carriers could be used to effect contact between the microorganism and the reagent mix. Test methodologies such as disk diffusion tests, the Etest, dilution methods, or automated microbiological analyzers can also be modified for the detection of antibiotic-inactivating enzymes without departing from the spirit and scope of the presently-disclosed subject matter.

Exemplary permeabilizing or lysis agents useful in the present invention include those agents that disrupt or increase the permeability of the membrane(s) and/or cell wall of a microorganism. As is well known to those of ordinary skill in the art, not all microorganisms have both a membrane and cell wall, moreover those that possess both are not necessarily structurally identical. For example, bacteria are broadly categorized as gram-positive or gram-negative based on their cell wall and membrane structure.

Other lysis agents include B-PER and the proteolytic enzyme, achromopeptidase. In some implementations, the permeabilizing or lysis agent is B-PER II Bacterial Protein Extraction Reagent (2×), commercially available from Thermo Scientific, Rockford, Ill. (catalog number 78260). As supplied, the B-PER II buffer is a solution containing a proprietary, nonionic detergent in 20 mM Tris.HCl; pH 7.5. In some embodiments, an undiluted solution of B-PER II Bacterial Protein Extraction Reagent is utilized.

With respect to the beta-lactam substrates used in accordance with the presently-disclosed methods, in some implementations, the beta-lactam substrate is imipenem, with cilastatin, for injection, USP (I.V.) 500 mg/500 mg per vial. This is provided as a powder which is reconstituted in the reagent solution used in the admixture.

With respect to the activators of beta-lactamases used in accordance with the presently-disclosed methods, in some implementations, the activator of metallo-beta-lactamases is zinc sulfate solution, 0.3 N, commercially available from Sigma-Aldrich Co., (catalog number Z2876), diluted 2 ml into 28 ml sterile, deionized water to provide a 15 mM stock solution.

With respect to the indicator used in accordance with the presently-disclosed methods, in some implementations, the indicator is phenol red indicator solution 0.5% (w/v), commercially available from Ricca Chemical Company, Batesville, Ind. (Supplier No. R5724500-500A). Use of an undiluted solution is acceptable.

With respect to the inhibitors used in accordance with the presently-disclosed methods, in some implementations, the inhibitor of class C (AmpC) beta-lactamases is sodium cloxacillin monohydrate commercially available from Sigma-Aldrich Co. (catalog number C9393), diluted 0.5 ml into 50 ml sterile, deionized water to provide a stock solution. Other specific examples of AmpC inhibitors include flucloxacillin, dicloxacillin, nafcillin, oxacillin, methicillin, and boronic acid.

In some implementations, the above-described ingredients are combined in appropriate quantities to make a stock test solution that is aliquoted into appropriate tubes such as provided in a clear 0.2 ml TempAssure PCR 8-tube strip, commercially available from USA Scientific (catalog number 1402-2700). In some embodiments, the ranges of quantities of the above-mentioned components are:

| | |
|---|---|
| B-PER II | 50-500 µl |
| Phenol Red | 50-140 µl |
| Zinc Sulfate | 5-45 µl |
| Cloxacillin | 300-2,000 µl |
| Imipenem/cilastatin | 1-90 mg |

In some embodiments of the tests described herein, glucose and thimerosal are further included as reagents in the test. In some embodiments, glucose accelerates the speed of the test, and hence its sensitivity. In some embodiments, the addition of glucose renders the test too sensitive and some false positive results occur. The problem of such false positives is overcome, in certain embodiments, by adding thimerosal to the test solution. It is appreciated that glucose is currently used in identification tests to distinguish between bacteria that utilize glucose and those that do not, and it is also incorporated into potato flake agar to induce sporulation by fungi. In the presently-disclosed subject matter, in some embodiments, the glucose increases the efficiency of carbapenemase enzymes. In some embodiments, polymyxin B is included in the test as a membrane active agent to enhance the release of intracellular carbapenemase enzymes to facilitate their interaction with the substrate.

Further provided, in other embodiments of the presently-disclosed subject matter, is a kit for detecting beta-lactamases. In some embodiments, a kit is provided that includes a permeabilizing or cell lysis agent, at least one beta-lactam, an indicator to detect beta-lactamase activity, one or more inhibitors to selectively inhibit certain classes of beta-lactamases, and any necessary activators of beta-lactamases.

Again, without wishing to be bound by any particular theory or mechanism, it is believed that the presently-disclosed subject matter provides novel benefits and advantages over other tests for the detection of beta-lactamases. In contrast to other current rapid phenotypic tests of this nature, the methods described herein can incorporate an inhibitor of class C beta-lactamases, which eliminates the need for a test control, enhances ease of interpretation, and eliminates falsely positive results. Compared to other current rapid phenotypic tests, the methods described herein can be, in certain implementations, a miniaturized test. This reduces the quantities required for test inoculum, reagents and space. In contrast to phenotypic tests requiring longer incubation periods, the speed of this test is an advantage, but other advantages, depending on which test it is compared to, may include superior sensitivity, specificity, convenience or economy of cost, space and technical time.

The presently-disclosed subject matter is further illustrated by the following specific but non-limiting Examples. Some of the following examples may be prophetic, notwithstanding the numerical values, results and/or data referred to and contained in the examples. Further, the following Examples may include compilations of data that are representative of data gathered at various times during the course of development and experimentation related to the present invention.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Determination of Detection of Antibiotic-Inactivating Factors at 37° C.

In this example, *Klebsiella pneumoniae* ATCC BAA 1705 (which produces a KPC class A carbapenemase and is a well-known positive control organism for carbapenemase detection tests) and *Klebsiella pneumoniae* ATCC BAA 1706 (which is a well-known negative control organism for carbapenemase detection tests) were harvested directly into separate tubes containing 25 µl aliquots of the test solution comprising the below quantities of the above-mentioned components:

| | |
|---|---|
| B-PER II | 140 µl |
| Phenol Red | 140 µl |
| Zinc Sulfate | 25 µl |
| Cloxacillin | 800 µl |
| Imipenem/cilastatin | 11 mg |

The contents were immediately mixed by repeated harvesting and twirling of the 1 µl loop with which the organisms were harvested and delivered into the test solution, and the tubes were placed in a 37° C. incubator. The color of the tube contents was monitored visually by being placed horizontally over a white background and inspected at intervals for up to 2 hours. The tube inoculated with *K. pneumoniae* ATCC BAA 1705 changed color from red to yellow (a positive test) in 5 minutes. The tube inoculated with *K. pneumoniae* ATCC BAA 1706 remained red (negative) for the duration of the experiment.

Example 2—Determination of Detection of Antibiotic-Inactivating Factors at Room Temperature The experiment in Example 1 was repeated with incubation at room temperature (25° C.). The tube inoculated with *K. pneumoniae* ATCC BAA 1705 changed color from red to yellow (a positive test) in 5 minutes. The tube inoculated with *K. pneumoniae* ATCC BAA 1706 remained red (negative) for the duration of the experiment.

Example 3—Determination of Detection of Antibiotic-Inactivating Factors at 37° C.

The experiment in Example 1 was repeated using *K. pneumoniae* ATCC BAA 1705 and *K. pneumoniae* ATCC BAA 1706 to investigate the impact of a variety of volumes of test components on the incubation time for a positive test result with *K. pneumoniae* ATCC BAA 1705. *K. pneumoniae* ATCC BAA 1706 yielded a negative result during each of these experiments.

| | |
|---|---|
| B-PER II | 250 µl |
| Phenol Red | 140 µl |
| Zinc Sulfate | 25 µl |
| Cloxacillin | 800 µl |
| Imipenem/cilastatin | 10 mg |

Incubation time for positive result: 30 minutes

Example 4—Determination of Detection of Antibiotic-Inactivating Factors at Room Temperature The experiment in Example 3 was repeated using *K. pneumoniae* ATCC BAA 1705 and *K. pneumoniae* ATCC BAA 1706 to investigate the impact of a variety of volumes of test components on the incubation time for a positive test result with *K. pneumoniae* ATCC BAA 1705. *K. pneumoniae* ATCC BAA 1706 yielded a negative result during each of these experiments. Incubation time for positive result: 30 minutes

Example 5—Determination of Detection of Class A Carbapenemase at 37° C.

The experiment in Example 1 was repeated in triplicate using *K. pneumoniae* ATCC BAA 1705 and *K. pneumoniae* with the second tubes for each organism supplemented with boronic acid and the third tube supplemented with EDTA. The unsupplemented tube and the tube supplemented with EDTA and inoculated with *K. pneumoniae* ATCC BAA 1705 changed color from red to yellow (a positive test) in 5 minutes. The tube supplemented with boronic acid and inoculated with *K. pneumoniae* ATCC BAA 1705 and the three tubes inoculated with *K. pneumoniae* ATCC BAA 1706 remained red (negative) for the duration of the experiment. These results indicated that *K. pneumoniae* ATCC BAA 1705 produced a carbapenemase that was inhibited by boronic acid but not by EDTA, i.e., a class A carbapenemase.

Example 6—Determination of Detection of Class A Carbapenemase at Room Temperature The experiment in Example 5 was repeated at room temperature. The unsupplemented tube and the tube supplemented with EDTA and inoculated with *K. pneumoniae* ATCC BAA 1705 changed color from red to yellow (a positive test) in 5 minutes. The tube supplemented with boronic acid and inoculated with *K. pneumoniae* ATCC BAA 1705 and the three tubes inoculated with *K. pneumoniae* ATCC BAA 1706 remained red (negative) for the duration of the experiment. These results indicated that *K. pneumoniae* ATCC BAA 1705 produced a carbapenemase that was inhibited by boronic acid but not by EDTA, i.e., a class A carbapenemase.

Example 7—Determination of Detection of Class B Carbapenemase (Metallo-Beta-Lactamase) at 37° C.

The experiment in Example 5 was repeated in triplicate using *E. coli* ATCC BAA 2452 (which produces a NDM class B carbapenemase and is a well-known positive control organism for carbapenemase detection tests) and *K. pneumoniae* with the second tubes for each organism supplemented with boronic acid and the third tube supplemented with EDTA. The unsupplemented tube and the tube supplemented with boronic acid and inoculated with *E. coli* ATCC BAA 2452 changed color from red to yellow (a positive test) in 10 minutes. The tube supplemented with EDTA and inoculated with *E. coli* ATCC BAA 2452 and the three tubes inoculated with *K. pneumoniae* ATCC BAA 1706 remained red (negative) for the duration of the experiment. These results indicated that *E. coli* ATCC BAA 2452 produced a carbapenemase that was inhibited by EDTA but not by boronic acid, i.e., a class B carbapenemase (metallo-beta-lactamase).

Example 8—Determination of Detection of Class B Carbapenemase (Metallo-Beta-Lactamase) at Room Temperature The experiment in Example 7 was repeated at room temperature. The unsupplemented tube and the tube supplemented with boronic acid and inoculated with *E. coli* ATCC BAA 2452 changed color from red to yellow (a positive test) in 10 minutes. The tube supplemented with EDTA and inoculated with *E. coli* ATCC BAA 2452 and the three tubes inoculated with *K. pneumoniae* ATCC BAA 1706 remained red (negative) for the duration of the experiment. These results indicated that *E. coli* ATCC BAA 2452 produced a carbapenemase that was inhibited by EDTA but not by boronic acid, i.e., a class B carbapenemase (metallo-beta-lactamase).

Example 9—Determination of Detection of Class D (OXA) Carbapenemase at 37° C.

The experiment utilizing the below quantities on the test solution was repeated in triplicate using *K. pneumoniae* 81 (which produces an OXA-48 class D carbapenemase) and *K. pneumoniae* ATCC BAA 1705, with the second tubes for each organism supplemented with boronic acid and the third tube supplemented with EDTA. All tubes inoculated with *K. pneumoniae* 81 changed color from red to yellow (a positive test) in 1 hour. All tubes inoculated with *K. pneumoniae* ATCC BAA 1706 remained red (negative) for the duration of the experiment. These results indicated that E *K. pneumoniae* 81 produced a carbapenemase that was not inhibited by EDTA or boronic acid, i.e., a class D carbapenemase.

| | |
|---|---|
| B-PER II | 200 µl |
| Phenol Red | 140 µl |
| Zinc Sulfate | 40 µl |
| Cloxacillin | 800 µl |
| Imipenem/cilastatin | 10 mg |

Example 10—Determination of Detection of Class D (OXA) Carbapenemase at Room Temperature The experiment in Example 9 was repeated at room temperature. All tubes inoculated with *K. pneumoniae* 81 changed color from red to yellow (a positive test) in 1 hour. All tubes inoculated with *K. pneumoniae* ATCC BAA 1706 remained red (negative) for the duration of the experiment. These results indicated that E *K. pneumoniae* 81 produced a carbapenemase that was not inhibited by EDTA or boronic acid, i.e., a class D carbapenemase.

Example 11—CPO Complete Diagnostic Criteria Test

Materials for CPO Complete Test

Three test solutions were used: A, B and C. Solution A was the test solution to detect carbapenemases. It can be used alone if detection is all that is required. Solutions B and C are supplements that are added to Solution A to classify carbapenemases into the categories of Class A, Class B, Class D or Carbapenemase Positive but Unclassified. The methodology is described below.

Use of Solution A for Carbapenemase Detection

30 µl of Solution A is dispensed into in three transparent vessels such as PCR tubes (VWR International catalog #20170-004) or wells in a microtiter tray (for convenience, the vessel is referred to as a tube from here on). The solution should be red prior to inoculation.

One vessel is for the test isolate. The other two are for a positive and a negative control isolate that should be run concurrently with the detection test. The control isolates are described below.

Colonies of the bacterial inoculum are harvested with a 1 µl loop (e.g., VWR International, catalog #12000-806) from an agar-based culture, typically blood agar (BD Diagnostics Systems, Sparks, Md.). The volume of inoculum should be sufficient to provide a slightly convex surface after filling the loop aperture (as opposed to a bulging loop with an excessive amount of inoculum). Excess inoculum should be avoided as it may reduce test accuracy. Testing may also utilize colonies harvested from selective and differential media such as, but not limited to, ChromID Carba agar (bioMérieux EU cat. No. 43861), ChromID OXA-48 agar (bioMérieux EU cat. No. 414011) and MacConkey agar (bioMérieux EU cat. No. 43141). Tests of lactose-fermenting colonies harvested from MacConkey agar may require a prewashing step to eliminate carryover of acid, which could interfere with test interpretation.

The inoculum is transferred from the 1 µl loop and suspended in the previously dispensed 30 µl of Solution A by rotating the loop vigorously in the test solution.

The test is then incubated on the bench top at room temperature and the result interpreted in bright light against a white background by comparison of the color of the inoculated test to the color of the negative control. A positive test is the development of yellow, orange or a lighter shade of red than the negative control (FIG. 1). The test result is valid if the positive control isolate yields a positive test.

The control isolates are as follows:

Positive control—one of *Klebsiella. pneumoniae* BAA 1705 (KPC), *K. pneumoniae* BAA 2452 (NDM-1), *K. pneumoniae* G15491 (OXA-181). Preferably, these are used on a rotational basis.

Negative control—*Klebsiella aerogenes* (formerly known as *Enterobacter aerogenes*) G1614.

The test is incubated until a positive result is obtained or for up to 90 minutes.

Use of Solutions A, B and C for Carbapenemase Detection and Classification

Solution B contains boronic acid, which is an inhibitor of Class A carbapenemases. Solution C contains two inhibitors of Class B carbapenemases. These are the chelating agents tris/EDTA and dipicolinic acid (pyridine-2,6-dicarboxylic acid). The recipes for preparation of the solutions are provided below.

Classification is achieved by testing an isolate concurrently in three tubes labelled A, B and C. Each tube contains 30 µl of Solution A. Two µl of Solution B is added to the second of the three tubes and is labeled "B", and two µl of Solution C is added to the third of the three tubes and is labeled "C". The remaining unsupplemented tube is labelled "A". Each tube is inoculated with the test isolate in the manner described above.

Carbapenemases may be classified only if tube A yields a positive result (i.e., the test isolate is carbapenemase-positive). Experiments in tubes B and C are interpreted as positive if the solution color changes from dark red to a lighter color. Changes of color in tubes B and C may be slower and less intense than for tube A. Therefore, interpretation should be based on which of tubes B or C is more positive (i.e., lighter in color). It is not necessary to use negative control strain G1614 as a definitive reference standard.

Interpretations are shown in Table 1. This guide is for isolates that produce a single carbapenemase. Rare isolates produce two carbapenemases.

A rapid, manual, phenotypic CPO detection and carbapenemase classification test, "CPO Complete", was developed, which is based on the detection of accelerated carbapenem hydrolysis. It can be adapted to current automated instruments. A study was designed to evaluate its speed and accuracy of CPO detection and its carbapenemase classification potential.

TABLE 1

Interpretation Guide for Carbapenemase Classification Tests

| Carbapenemase | Tube | | |
|---|---|---|---|
| Classification | A | B | C |
| Class A | Positive | Negative | Positive |
| Class B | Positive | Positive | Negative |
| Class D | Positive | Positive | Positive |
| Positive Untyped | Positive | Negative | Negative |
| Negative | Negative | Do not interpret | Do not interpret |

Recipes for Solutions

| Chemicals | Quantity |
|---|---|
| Solution A (test is performed in 30 µl volume) | |
| Thimerosal (Enzo cat. no. ALX-400-013-G005) | 100 mg |
| Imipenem/cilastatin (Hospira cat. no. NDC 0409-3507-21) | 120 mg |
| Glucose (Sigma cat no. G-5000) | 50 mg |
| Polymyxin B Sulfate (EMD Millipore Corp., USA, cat. no. 5291-500 MG) | 40 mg |
| Zinc Sulfate (Sigma-Aldrich Co. cat. no Z2876) | 300 µl |
| Mueller-Hinton broth (Oxoid, UK, cat no CM0405) | 10 ml |
| Phenol Red (VWR International catalog # 97062-476) | 1,400 µl |
| pH adjusted to 7.0 using concentrated NaOH & HCl | |
| Total Volume | 11.7 ml |
| Solution B (test is performed in 30 µl of Solution A plus 2 µl of Solution B) | |
| Phenyl boronic acid (VWR International catalog # BT130960-10G) | 120 mg |
| Dimethyl Sulfoxide (VWR International catalog # BDH1115-1LP) | 3 ml |
| Sterile inoculum water (Beckman Coulter, Inc. Brea, CA, cat no B1015-2)) | 3 ml |
| Phenol Red (VWR International catalog # 97062-476) | 840 µl |
| pH adjusted to 7.5 using concentrated NaOH & HCl | |
| Total Volume | 6.84 ml |
| Solution C (test is performed in 30 µl of Solution A plus 2 µl of Solution C) | |
| Tris-EDTA buffer solution 100x concentrate (Sigma T9285) | 10 ml |
| Pyridine-2,6-dicarboxylic acid, 98% (aka dipicolinic acid) (Alfa Aesar cat no A12263) | 235 mg |
| Phenol Red (VWR International catalog # 97062-476) | 1400 µl |
| pH adjusted to 6.8 using concentrated NaOH & HCl | |
| Total Volume | 11.4 ml |

Example 12—Accelerated Carbapenemase Detection and Classification with Carbapenemase-Producing Organisms (CPO)

The global spread and high mortality of infections caused by carbapenemase-producing organisms (CPOs) can be attributed to ineffective infection control and failures to provide timely, effective therapy. Rapid CPO detection, coupled with classification of carbapenemases, can have multiple benefits. Rapid detection can play a role in reducing mortality and improving infection control efforts. Carbapenemase classification also can help to reduce mortality and can improve antibiotic stewardship by indicating if new beta-lactamase inhibitor combinations such as ceftazidime/avibactam and meropenem/vaborbactam are potential therapeutic candidates or are contraindicated. The combination of carbapenemase detection and classification can help to avoid overuse of these agents and thereby retard the development of resistance to them.

Methods

Isolates. The isolates consisted of 330 Enterobacteriaceae, *Pseudomonas aeruginosa* and *Acinetobacter baumannii* previously characterized for beta-lactamase production. Detection tests were performed on 125 isolates producing KPC, NMC-A, or SME class A carbapenemases, 87 isolates producing NDM, GIM, SPM, IMP or VIM class B carbapenemases, 46 isolates producing class D carbapenemases comprising OXA-48-like or *Acinetobacter*-associated OXAs, 5 isolates producing 2 carbapenemase classes and 67 non-CPOs. Classification potential was assessed for 206 CPOs producing a single carbapenemase class.

Carbapenemase detection. Colonies were suspended in a 30 µl volume of the carbapenemase accelerator solution and incubated on the bench top at room temperature. The test was interpreted in bright light against a white background by comparing the color of the test to the negative control. A positive test was interpreted as the development of yellow, orange or a lighter shade of red than the negative control (FIG. 1).

Carbapenemase classification. Colonies were suspended in three tubes—the carbapenemase accelerator solution alone (tube A) and the accelerator solution supplemented with phenotypic markers that differentiated between the molecular classes of the carbapenemases (tubes B and C). The tube B solution suppressed the activity of Class A carbapenemases and the tube C solution suppressed the activity of Class B carbapenemases. Tests with the phenotypic marker solutions were scored as positive or negative by interpreting visually for a reduction in the intensity of the initial dark red color. Table 1 below shows the interpretation scheme used for carbapenemase classification.

TABLE 1

Guide to Interpretation of Carbapenemase Classification Tests

| Classification | Solution A | Solution B | Solution C |
|---|---|---|---|
| Class A | Positive | Negative | Positive |
| Class B | Positive | Positive | Negative |
| Class D | Positive | Positive | Positive |
| Positive Untyped | Positive | Negative | Negative |
| Negative | Negative | Non-CPO NA* | Non-CPO NA* |

*classification not applicable

TABLE 2

CPO Detection and Classification Test Results

| DETECTION | No. of Isolates | Positive | Negative |
|---|---|---|---|
| Class A | 125 | 125 | 0 |
| Class B | 87 | 87 | 0 |
| Class D | 46 | 46 | 0 |
| Dual Types* | 5 | 5 | 0 |
| All CPOs | 263 | 263 (100%) | 0 (0%) |
| Non-CPOs | 67 | 1 (1.5%) | 66 (98.5%) |

| CLASSIFICATION | Correct | Incorrect or Unclassified |
|---|---|---|
| Class A | 98 | 98 | 0 |
| Class B | 63 | 63 | 0 |
| Class D | 45 | 42 | 3 |
| All | 206 | 203 (98.5%) | 3 (1.5%) |

TABLE 3

Detection Time for Positive Tests

| Minutes | Class A | Class B | Class D | Dual Types* | Total | Percent |
|---|---|---|---|---|---|---|
| 10 | 112 (89.6%) | 65 (74.7%) | 14 (30.4%) | 4 | 195 | 74.1% |
| 30 | 124 (99.2%) | 76 (87.4%) | 33 (71.7%) | 5 | 238 | 90.0% |
| 60 | 125 (100%) | 86 (98.9%) | 42 (91.3%) | 5 | 258 | 98.1% |
| 90 | 125 (100%) | 87 (100%) | 46 (100%) | 5 | 263 | 100% |
| Total | 125 | 87 | 46 | 5 | 263 | |

Figure 2:
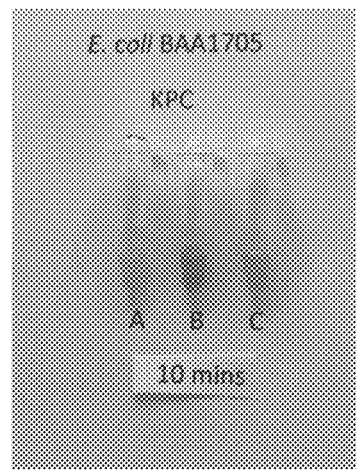
FIG. 2. Representative classification test for Class A carbapenemase-producing organism (CPO), KPC-producing *E. coli* BAA 1705 after 10 minutes incubation. Tubes A and C are positive (yellow). Tube B is negative (red). Tube A contains only the admixture and indicates that the isolate is carbapenemase-positive. Tubes B and C contain inhibitors that suppress Class A and B carbapenemases, respectively.
Figure 3:
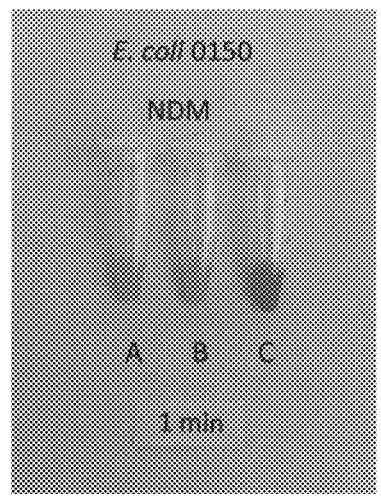
FIG. 3. Representative classification test for Class B CPO, NDM-producing *E. coli* 0150 after 1 minute incubation. This is the typical class B profile with positive results in tubes A and B and a negative result in tube C.
Figure 4:
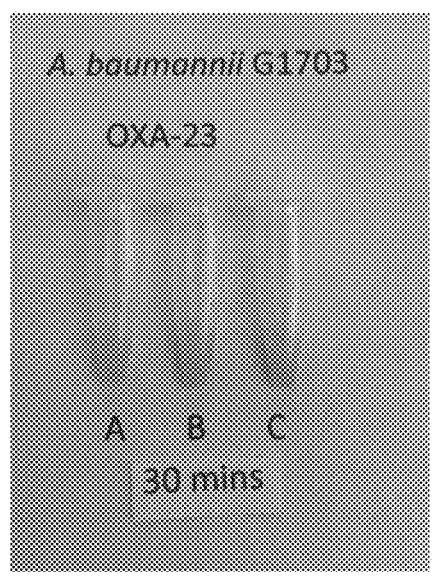
FIG. 4. Representative classification test for Class D CPO, OXA-23-producing *A. baumannii* G1703 after 30 minutes incubation. This is the typical class D profile with positive results in all three tubes.

*dual carbapenemase types, only 5 isolates tested - percent positive not calculated Results Carbapenemase Detection. All 263 CPOs yielded positive tests (100% sensitivity) and only one of the 67 non-CPOs yielded a falsely positive result (98.5% specificity) (Table 2). The carbapenemases of 74.1% of the CPOs were detected within seconds to 10 minutes and 98.1% were detected within 1 hour (Table 3). Notably, KPCs in *P. aeruginosa* were detected within 1 minute, 91.3% of OXA carbapenemases within 60 minutes, and KPC was detected in *A. baumannii*. Other notable indicators of high sensitivity were detection of *K. pneumoniae* KPC-4 production and *Proteus mirabilis* IMP-27 production. The single false positive result occurred with an AmpC-producing isolate of *Klebsiella aerogenes* (formerly *Enterobacter aerogenes*). Carbapenemase Classification. As shown in Table 2, all class A and B carbapenemases were correctly classified and 42 of the 45 class D carbapenemases were correctly classified. One class D carbapenemase producer yielded a positive but unclassified result and two class D producers were misclassified as class B carbapenemase producers. FIGS. 2-4 show representative classification test results obtained with isolates of KPC-producing *E. coli*, NDM-producing *E. coli* and OXA-23-producing *A. baumannii*.

Summary. With 100% sensitivity, 98.5% specificity, and 98.1% of CPOs detected within 1 hour, plus carbapenemase classifications, "CPO Complete" has the speed, accuracy and convenience to help improve patient management and reduce the mortality of CPO infections. Its ability to accurately detect and discriminate between Class A and Class B CPOs also provides the potential to help avoid overuse of ceftazidime/avibactam and meropenem/vaborbactam for ESBL and AmpC-associated infections that could be treated by other classes of antibiotics. This would help preserve the effective lives of these and similar anti-CPO agents. With lyophilized test storage possible at room temperature, the test provides a convenient and accurate diagnostic tool that can be utilized in efforts to control the currently escalating CPO pandemic.

Example 13—Additional Experimental Results

Based on its promise for use with positive blood cultures, the test described herein has the potential to be used for rapid detection of carbapenemase-producing pathogens in a variety of liquid culture media and liquid clinical samples, e.g., liquid culture media (e.g., enrichment broths, susceptibility test broths, general growth broths) or clinical samples (e.g., urine, cerebrospinal fluid, blood, exudates (e.g. transudate, ulcer), peritoneal fluid, pleural fluid, suprapubic aspirate, abscess, pus). In addition, tissue samples can be tested directly or inoculated into liquid growth media (e.g., see above).

As described in more detail below, the methods described herein can be used for rapid follow-up of positive blood cultures; or detection of carbapenemases in bacteria grown on chromagar and MacConkey agar media.

Rapid Follow-Up of Positive Blood Cultures

This utility has significant life-saving potential. Bacterial infections that spread to the blood stream have high, rapid mortality unless effective antibiotic therapy is quickly commenced. It is estimated that the mortality rate increases 11% for each hour that appropriate antibiotic therapy is delayed.

Traditionally it takes about 18-48 hours to obtain antibiotic susceptibility results from the laboratory after a blood culture becomes positive. Physicians typically prescribe "best guess" empirical antibiotic therapy during this delay while awaiting definitive antibiotic susceptibility results. With antibiotic resistance increasing, this approach is becoming increasingly unreliable.

Some hospitals utilize FDA-approved rapid molecular (e.g., Nanosphere Verigene microarray system) and/or phenotypic (e.g. Accelerate Pheno system) tests to follow up positive blood cultures. These detect some antibiotic resistance mechanisms and/or yield antibiotic susceptibility results within 2-8 hours. Both technologies are expensive and have limitations in accuracy or spectrum of coverage. For this reason, some laboratories choose to use conventional tests to check the accuracy of results produced by these technologies, thereby increasing the cost of testing.

The test described herein has the potential to detect and classify the carbapenemases of pathogens in positive blood cultures within minutes to an hour. Using such a test on spiked blood cultures, it has detected and classified carbapenemase-producing bacteria within 6 minutes to one hour.

Experiments have been conducted that simulated positive blood cultures by adding blood and carbapenemase-producing bacteria. When the blood culture instrument signals that a bottle is positive, it is removed and an aliquot (currently one ml) is centrifuged and tested as described herein.

Detection of Carbapenemases in Bacteria Grown on Chromagars, MacConkey Agar and Other Selective/Differential Media Other carbapenemase tests are inaccurate when performed using colonies harvested from chromagar and MacConkey agar media. Preliminary testing indicates that this is not an issue with the test described herein for colonies harvested from chromagars. Colonies of some acid-producing organisms harvested directly from MacConkey agar may require a washing step to prevent carryover of acid before testing.

| Recipe for Adding Ingredients to 1 ml of Mueller-Hinton broth | | |
|---|---|---|
| Ingredient | Optimal | Range |
| Mueller-Hinton broth (MHB) | 1 ml | 5%-100% concentration of MHB can be used |
| Zinc Sulfate | 30 µl | 5-45 µl |
| Phenol red | 140 µl | 40-150 µl |
| Thimerosal | 10 mg | 5-20 mg |
| Imipenem/cilastatin | 12 mg | 8-18 mg |
| Glucose | 5 mg | 0.12-12.0 mg |
| Polymyxin B | 4 mg | 8.4-75 mg |
| Solution A | pH 7.0 | pH 6.7-7.5 |
| Solution B | pH 7.5 | pH 6.7-8.5 |
| Solution C | pH 6.8 | pH 6.3-7.4 |

| Test Ingredients in 1 ml - pH values, Volumes of Liquids, Concentrations of Solids | | |
|---|---|---|
| Ingredient | Optimal | Range |
| Mueller-Hinton broth (MHB) | 0.85 ml | 5%-100% concentration of MHB can be used |
| Zinc Sulfate | 25.6 µl | 4.3-39 µl |
| Phenol red | 120 µl | 34.2-128 µl |
| Thimerosal | 8.55 mg/ml | 4.3-17 mg/ml |
| Imipenem/cilastatin | 10.25 mg/ml | 7-15 mg/ml |
| Glucose | 4.3 mg/ml | 0.1-10 mg/ml |
| Polymyxin B | 3.4 mg/ml | 8-64 mg/ml |
| Solution A | pH 7.0 | pH 6.7-7.5 |
| Solution B | pH 7.5 | pH 6.7-8.5 |
| Solution C | pH 6.8 | pH 6.3-7.4 |

Example 14—References

All publications, patents, and patent applications mentioned in this specification are herein incorporated by reference to the same extent as if each individual publication, patent, or patent application was specifically and individually indicated to be incorporated by reference, including the references set forth in the following list:

1. Thomson, 2010, J. Clin. Microbiol., 48:1019-25
2. Tzouvelekis et al., 2014, Clin. Microbiol. Infect., 20:862-72
3. Tofas et al., 2016, Int. J. Antimicrob. Agents, 47:335-39
4. Chauchereau et al., 1990, Analyt. Biochem., 188:310-6
5. Gill et al., 1981, J. Clin. Microbiol., 14:437-40
6. Oberhofer et al., 1982, J. Clin. Microbiol., 15:196-9
7. O'Callaghan et al., 1972, AAC, 1:283-8
8. Lacey et al., 1977, J. Clin. Pathol., 30:35-9
9. Gota, 1945, Science, 102:309
10. Andremont et al., 1982, Proc. Reun. Interdisc. Chim. Antiinfect. Soc. Francaise de Microbiol. Paris, 50
11. Kjellander et al., 1964, Acta Patholog. Microboil. Scandinavica, 61:494
12. Hodge et al., 1978, J. Clin. Microbiol., 7:102-3
13. Lee et al., 2001, Clin. Microbiol. Infect., 7:88-91
14. Jorgensen, 1985, Chemother., 31:95-101
15. Reig et al., 1984, Eur. J. Clin. Microbiol., 3:561-3
16. Doyle et al., 2012, J. Clin. Microbiol., 50:3877-80
17. Sanders et al., 1979, AAC, 15:792-7
18. Bush et al., 1995, AAC, 39:1211-33
19. Bush et al., 2010, Antimicrob. Agents Chemother., 54:969-76
20. Brun-Buisson et al, 1987, Lancet, ii:302-6
21. Brown et al., 2000, J. Antimicrob. Chemother., 46:327-8
22. Cormican et al., 1996, JCM, 34:1880-4
23. Ho et al., 1998, JAC, 42:49-54
24. Moland et al., 1998, JCM, 36:2575-9
25. Sanders et al., 1996, JCM, 34:2997-3001
26. Schooneveldt et al., 1998, Pathol., 30:164-168
27. Thomson et al., 1999, Antimicrob. Agents Chemother., 43:1393-1400
28. Thomson et al., 1984, J. Antimicrob. Chemother., 13:45-54
29. Thomson et al., 1992, AAC, 36:1877-82
30. Black et al., 2005, J. Clin. Microbiol., 43:3110-3
31. Clinical and Laboratory Standards Institute, 2015, Performance standards for antimicrobial susceptibility testing: $25^{th}$ informational supplement M100-S25, Clinical and Laboratory Standards Institute, Wayne, Pa.
32. Moland et al., 2008, Clin. Microbiol. Newsletter, 30:79-84

33. Kim et al., 2007, J. Clin. Microbiol., 45:2798-801
34. Doi et al., 2008, J. Clin. Microbiol., 46:4083-6
35. Tijet et al., 2016, J. Antimicrob. Chemother., 71:274-6
36. Nordmann et al., 2012, J. Clin. Microbiol., 50:3016-22
37. Dortet et al., 2014, J. Med. Microbiol., 63:772-6
38. Nordmann et al., 2012, Emerg. Infect. Dis., 18:1503-7
39. Tijet et al., 2013, Antimicrob. Agents Chemother., 57:4578-80
40. Papagiannitsis et al., 2015, J. Clin. Microbiol., 53:1731-5
41. Huang et al., 2014, J. Clin. Microbiol., 52:3060-3
42. Simner et al., 2015, J. Clin. Microbiol., 53:105-12
43. AbdelGhani et al., 2015, J. Clin. Microbiol., 53:3539-42
44. Kabir et al., 2016, J. Antimicrob. Chemother. 71:1213-6
45. Garg et al., 2015, Antimicrob. Agents Chemother., 59:7870-2
46. Hombach et al., 2015, J. Clin. Microbiol., 53:3828-33
47. Pires et al., 2013, J. Clin. Microbiol., 51:4281-3
48. Novais et al., 2015, J. Clin. Microbiol., 53:3105-7
49. Pasteran et al., 2015, JCM, 53:1996-8
50. Garcia-Fernandez et al., 2016, J. Clin. Microbiol., 54:464-6
51. Oueslati et al., 2015, J. Antimicrob. Chemother., 70:1059-63

It will be understood that various details of the presently disclosed subject matter can be changed without departing from the scope of the subject matter disclosed herein. Furthermore, the foregoing description is for the purpose of illustration only, and not for the purpose of limitation.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method for rapidly detecting whether or not a microorganism produces a beta-lactamase, comprising:
   incubating an admixture for a period of time under appropriate conditions, the admixture comprising the microorganism, a beta-lactam antibiotic, thimerosal, glucose, polymyxin B, and an indicator; and
   determining the presence, absence and/or status of the indicator, thereby determining whether or not the microorganism produces a beta-lactamase.

2. The method of claim 1, wherein the beta-lactamase is a carbapenemase.

3. The method of claim 2, wherein the microorganism is selected from the group consisting of members of the family Enterobacteriaceae, *Pseudomonas* spp., *Acinetobacter* spp., *Stenotrophomonas maltophilia, Bacteroides* spp., *Bacillus cereus*, and *Aeromonas* spp.

4. The method of claim 1, wherein the indicator is selected from the group consisting of phenol red, bromothymol blue, neutral red, naphtholphthalien, and cresol red.

5. The method of claim 1, wherein the admixture further comprises an activator of a beta-lactamase.

6. The method of claim 5, wherein the activator comprises zinc sulfate.

7. The method of claim 1, wherein the determining step occurs within 1 hour of the start of the incubating step.

8. The method of claim 1, wherein the determining step occurs within 10 minutes of the start of the incubating step.

9. The method of claim 1, further comprising comparing the presence, absence and/or status of the indicator to a negative control comprising *Klebsiella aerogenes*.

* * * * *

UNITED STATES PATENT AND TRADEMARK OFFICE
CERTIFICATE OF CORRECTION

PATENT NO. : 11,492,653 B2
APPLICATION NO. : 16/638429
DATED : November 8, 2022
INVENTOR(S) : Gina K. Thomson, Kenneth S. Thomson and Sameh Mohamed Mohamadi AbdelGhani It is certified that error appears in the above-identified patent and that said Letters Patent is hereby corrected as shown below:

In the Claims

Column 28, Line 26, Claim 3, delete "Enterobacteriaceae," and insert -- *Enterobacteriaceae*, --

Column 28, Line 31, Claim 4, delete "naphtholphthalien," and insert -- naphtholphthalein, --

Signed and Sealed this
Twenty-seventh Day of December, 2022

*Katherine Kelly Vidal*

Katherine Kelly Vidal
*Director of the United States Patent and Trademark Office*